(12) United States Patent
Shigemori et al.

(10) Patent No.: US 12,121,543 B2
(45) Date of Patent: Oct. 22, 2024

(54) METHOD FOR PRODUCING PLATELETS USING RECIPROCATING STIRRING DEVICE

(71) Applicants: Megakaryon Corporation, Kyoto (JP); Satake Chemical Equipment MFG., LTD., Saitama (JP)

(72) Inventors: Tomohiro Shigemori, Kyoto (JP); Haruki Okamoto, Kyoto (JP); Yoshikazu Kato, Saitama (JP)

(73) Assignee: Megakaryon Corporation, Kyoto (JP)

( * ) Notice: Subject to any disclaimer, the term of this patent is extended or adjusted under 35 U.S.C. 154(b) by 957 days.

(21) Appl. No.: 15/773,099

(22) PCT Filed: Oct. 31, 2016

(86) PCT No.: PCT/JP2016/082206
§ 371 (c)(1),
(2) Date: May 2, 2018

(87) PCT Pub. No.: WO2017/077964
PCT Pub. Date: May 11, 2017

(65) Prior Publication Data
US 2018/0318352 A1 Nov. 8, 2018

(30) Foreign Application Priority Data
Nov. 2, 2015 (JP) .................... 2015-215936

(51) Int. Cl.
*C12M 1/06* (2006.01)
*A61K 35/19* (2015.01)
(Continued)

(52) U.S. Cl.
CPC ............ *A61K 35/19* (2013.01); *A61K 35/545* (2013.01); *C12M 1/02* (2013.01); *C12M 3/08* (2013.01);
(Continued)

(58) Field of Classification Search
CPC ...................................... C12M 27/02
See application file for complete search history.

(56) References Cited

U.S. PATENT DOCUMENTS 6,491,422 B1 * 12/2002 Rutten ............... B01F 11/0258
366/116
9,095,828 B2 * 8/2015 Mennenga ............ B01F 31/449
(Continued)

FOREIGN PATENT DOCUMENTS

EP 2298865 A 3/2011
JP 4316251 B2 8/2009
(Continued)

OTHER PUBLICATIONS

1 Thon et al., "Platelet bioreactor-on-a-chip," Blood, 124: 1857-1867 (2014).
(Continued)

*Primary Examiner* — Jonathan M Hurst
(74) *Attorney, Agent, or Firm* — Morgan, Lewis & Bockius LLP (57) ABSTRACT

The present invention provides a method for producing platelets, including the step of culturing megakaryocyte cells in a culture solution in a culture vessel, wherein in the culturing step, the culture solution is stirred by a stirring blade moving reciprocally.

15 Claims, 9 Drawing Sheets

(51) Int. Cl.
*A61K 35/545* (2015.01)
*C12M 1/00* (2006.01)
*C12M 1/02* (2006.01)
*C12M 1/36* (2006.01)
*C12M 3/08* (2006.01)
*C12N 5/10* (2006.01)
*C12N 5/16* (2006.01)
*C12N 15/85* (2006.01)
*C12M 3/00* (2006.01)
*C12N 15/09* (2006.01)

(52) U.S. Cl.
CPC ............ *C12M 21/00* (2013.01); *C12M 27/00* (2013.01); *C12M 29/00* (2013.01); *C12M 41/48* (2013.01); *C12N 5/10* (2013.01); *C12N 5/16* (2013.01); *C12N 15/85* (2013.01); *C12M 3/00* (2013.01); *C12N 15/09* (2013.01); *C12N 2015/8572* (2013.01)

(56) References Cited

U.S. PATENT DOCUMENTS

| | | | | |
|---|---|---|---|---|
| 10,092,888 | B2* | 10/2018 | Barksdale | B01F 33/4534 |
| 2005/0249033 | A1* | 11/2005 | Krause | B01F 31/441 |
| | | | | 366/332 |
| 2007/0243608 | A1* | 10/2007 | Kyba | C12N 5/0644 |
| | | | | 435/325 |
| 2009/0116335 | A1* | 5/2009 | Wild | B01F 35/4111 |
| | | | | 366/249 |
| 2011/0026361 | A1* | 2/2011 | Sato | B01F 11/0082 |
| | | | | 366/343 |
| 2011/0053267 | A1 | 3/2011 | Nakauchi et al. | |
| 2011/0058448 | A1* | 3/2011 | Reif | B01F 35/513 |
| | | | | 366/250 |
| 2011/0065190 | A1 | 3/2011 | Nakano et al. | |
| 2012/0238023 | A1* | 9/2012 | Eto | A61P 7/06 |
| | | | | 435/467 |
| 2014/0127815 | A1 | 5/2014 | Eto et al. | |
| 2016/0002599 | A1 | 1/2016 | Eto | |
| 2016/0022736 | A1 | 1/2016 | Feng et al. | |
| 2018/0251718 | A1* | 9/2018 | Labruzzo | C12M 27/16 |

FOREIGN PATENT DOCUMENTS

| | | |
|---|---|---|
| JP | 2009-297023 A | 12/2009 |
| JP | 2016-021908 A | 2/2016 |
| WO | 2009/122747 A1 | 10/2009 |
| WO | 2012/157586 A1 | 11/2012 |
| WO | 2014/100779 A1 | 6/2014 |
| WO | 2014/123242 A1 | 8/2014 |

OTHER PUBLICATIONS

Feng et al., "Scalable Generation of Universal Platelets from Human Induced Pluripotent Stem Cells", Stem Cell Reports, 3:817-831 (2014).

Website of Satake Chemical Equipment Mfg., Ltd., Satake Vmove Mixer (online), Sep. 23, 2015. [searched on Jan. 10, 2017].

Nakamura et al., "Expandable Megakaryocyte Cell Lines Enable Clinically Applicable Generation of Platelets from Human Induced Pluripotent Stem Cells", Cell Stem Cell, 14:535-548 (2014).

Harimoto et al., "Towards Industrialization: Development of Ips Cell-derived Platelet Production System", Tissue Eng., Part A, 21: Suppl. I, S-15 (2015).

International Search Report issued in corresponding International Patent Application No. PCT/JP2016/082206 .

* cited by examiner

Fig. 6
MEASUREMENT OF BIOACTIVITY (PAC-1) OF PLATELETS

Fig. 8

MEASUREMENT OF ABNORMAL PLATELETS

Fig. 9

METHOD FOR PRODUCING PLATELETS USING RECIPROCATING STIRRING DEVICE

TECHNICAL FIELD

The present invention relates to a method for producing platelets using a stirring device including a stirring blade that moves reciprocally.

BACKGROUND ART

A platelet preparation is administered to subjects who lost a large amount of blood in operations or injuries or who has a bleeding tendency with a reduction of platelets after anticancer drug treatments, in order to treat or prevent the symptoms. The production of platelet preparation currently depends on blood donation by healthy volunteers. However, the number of blood donors is reducing because of the composition of population in Japan, and it is estimated that a shortage of donated blood of about a million people will occur in 2027. Thus, stable supply of platelets is one of the purposes in the technical field of the present invention.

Moreover, a conventional platelet preparation has a high risk of microbial contamination. Thus, serious infectious diseases may be caused after transfer of the platelet preparation. Thus, more safety platelet preparations are always required in clinical sites. To meet the need, a method for producing platelets from megakaryocyte cells cultured in vitro is developed nowadays.

Platelets have been conventionally produced from cultured cells in a static culture system using a dish (WO 2014/100779 A1, Qiang Feng, et al., Stem Cell Reports). However, the production in the static culture system takes a lot of trouble and is unsuitable for mass culture.

CITATION LIST

Patent Document

Patent Document 1: WO 2014/100779 1

Non-Patent Document

Non-Patent Document 1: Qiang Feng, et al., Stem Cell Reports 3 1-15 (2014)

SUMMARY

Technical Problem

The inventors of the present invention succeeded in producing platelets having a high bioactivity by using a culture method in a shaking culture system using a shaker flask, i.e., including shaking a culture vessel itself. However, it was revealed that the production amount of platelets (CD41a+CD42b+) and bioactivity (PAC1 binding property, P-selectin positive) of platelets are reduced in the shaking-flask culture system in accordance with scale-up of the medium amount.

Moreover, it was found that a degradation reaction (reduction in CD42b positive rate) of platelets, considered to be caused by a shedding reaction occurs in the shaking-flask culture system. Furthermore, it is found that the platelets contain many abnormal platelets (annexin V-positive platelets) that are unsuitable for transfer to biological bodies.

Hence, the present invention is intended to provide a method for producing a large amount of high-quality platelets that can be transferred to biological bodies.

Solution to Problem

The inventors of the present invention conducted earnest studies to solve the problem. As a result of the earnest studies, the inventors of the present invention found that the production efficiency and bioactivity of platelets can be increased, degradation of platelets can be inhibited, and abnormal platelets can be reduced, by culturing megakaryocyte cells while reciprocally moving a stirring blade arranged in a culture vessel to stir a culture solution without shaking the culture vessel. Furthermore, the inventors of the present invention conducted studies on other conditions such as cell density at the time of stirring culture using a reciprocating stirring device and completed the present invention.

That is, the present invention provides a method for producing platelets, which includes: a culturing step of culturing megakaryocyte cells in a culture solution in a culture vessel, wherein in the culturing step, the culture solution is stirred by using an unsteady stirring device in which a stirring blade does not move in one direction but moves reciprocally or is inverted.

In the method for producing platelets, according to the present invention, the culture vessel is preferably a closed bioreactor.

In the method for producing platelets, according to the present invention, the megakaryocyte cells are preferably obtained by subjecting, to forced expression, at least one selected from the group consisting of cancer genes, Polycomb genes, and apoptosis inhibitory genes in cells before being differentiated into megakaryocyte cells, and then cancelling the forced expression.

The present invention further provides a method for producing a platelet preparation, which includes: the step of producing platelets in megakaryocyte cells by the above-described method, and collecting the platelets from a culture; and the step of removing a hematopoietic cell component other than platelets from the platelets.

The present invention further provides a method for producing a blood preparation, which includes: producing step of producing a platelet preparation by the above-described method; and the obtaining step of mixing the platelet preparation and another component to obtain a blood preparation.

The present invention is platelets produced by any of the above-described methods.

The present invention further provides a platelet preparation produced by any of the above-described methods or a platelet preparation containing the platelets.

The present invention is a blood preparation produced by the above-described method or a blood preparation containing the platelets.

Advantageous Effects of Invention

The method of the present invention can further improve the production efficiency of platelets compared with conventional shaking culture. Moreover, the platelets produced by the method of the present invention has a higher bioactivity than those produced by the conventional shaking culture.

The method of the present invention can inhibit the degradation reaction (reduction in CD42b positive rate) of platelets and can also inhibit production of abnormal platelets (annexin V-positive platelets).

DESCRIPTION OF EMBODIMENTS

The method for producing platelets according to the present invention includes: a culturing step of culturing megakaryocyte cells in a culture solution in a culture vessel, and in the culturing step, the culture solution is stirred by using an unsteady stirring device in which a stirring blade does not move in one direction but moves reciprocally or is inverted. For example, the culture solution may be stirred with the stirring blade so that the stirring blade may have a resistance of a fluid to the main surface. More preferably, the stirring blade moves reciprocally in the support shaft direction. More preferably, the culture vessel is stand still, a support shaft that supports the stirring blade moves reciprocally in the direction in which the support shaft extends to move the stirring blade in the vertical direction.

In the present specification, the "culture vessel" is a container capable of culturing megakaryocyte cells while stirring a culture solution with a reciprocating stirring device and is not limited to particular vessels. Examples of the culture vessel include a culture dish in an open system, a flask with a screwed cap in a close system, and a bioreactor (including a closed bioreactor).

In the present specification, the "stirring blade" is only necessary to be capable of being arranged in the culture solution and directly stirring the culture solution. As the stirring blade, a plate-shaped stirring blade or a stirring blade having a bending structure is used, for example.

The following describes an example using a bioreactor 10 including a stirring blade as an embodiment of the present invention.

Figure 1:
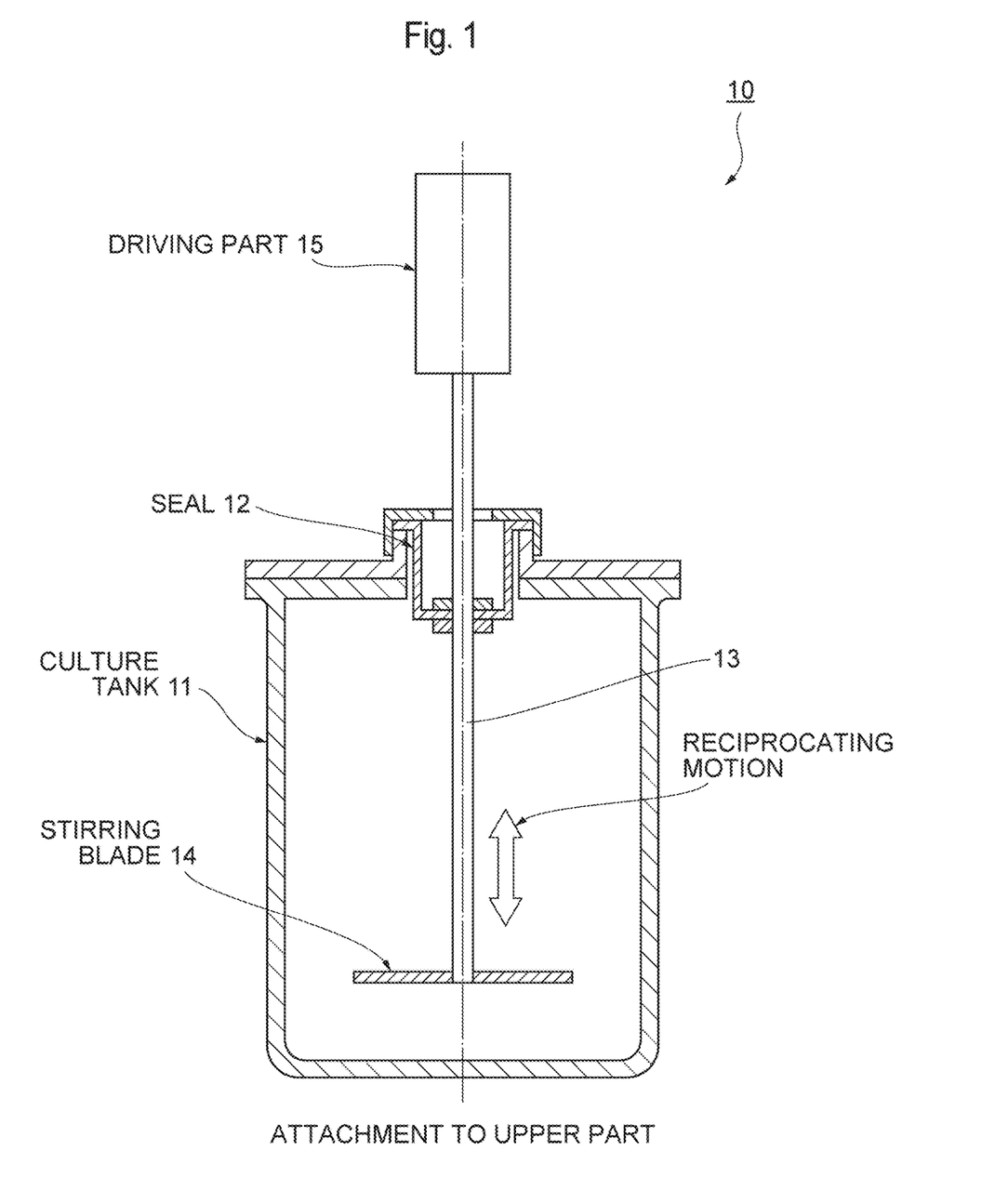
FIG. 1 shows a bioreactor according to an embodiment of the present invention.
Figure 2:
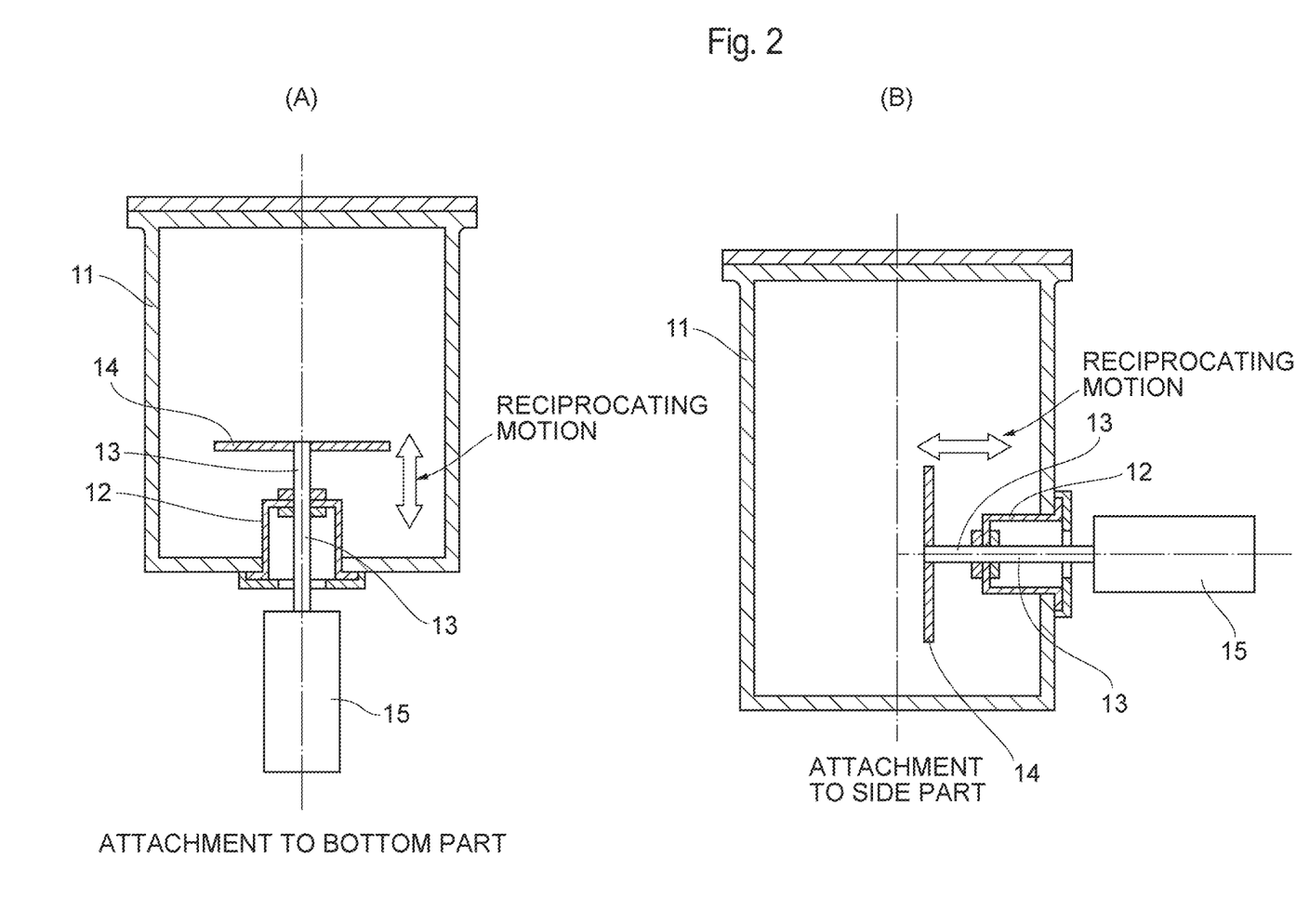
FIG. 2 shows placement examples of a seal, a driving shaft, a stirring blade in the bioreactor according to the embodiment of the present invention.
Figure 3:
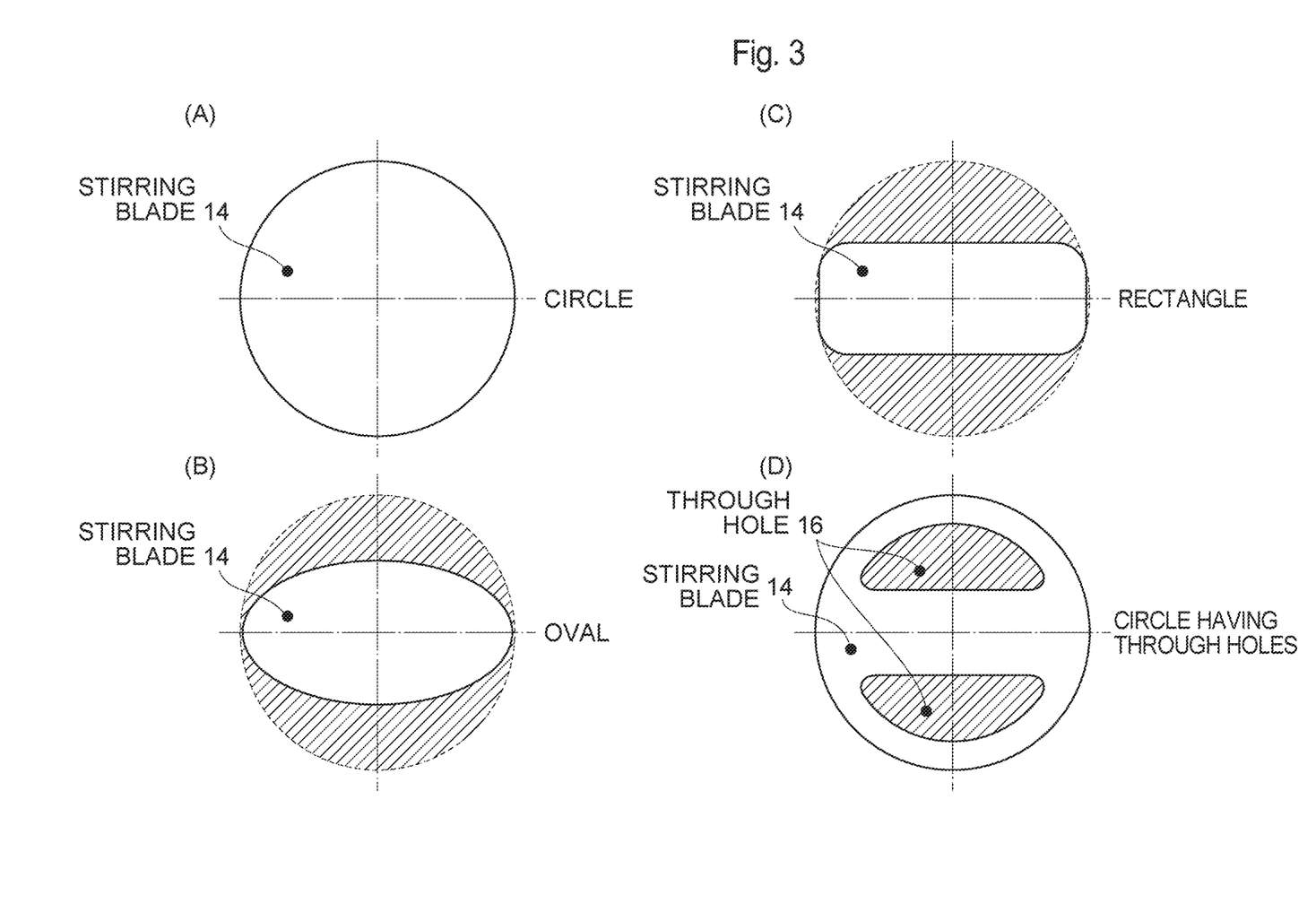
FIG. 3 shows structures of the stirring blade in the bioreactor according to the embodiment of the present invention.
Figure 9:
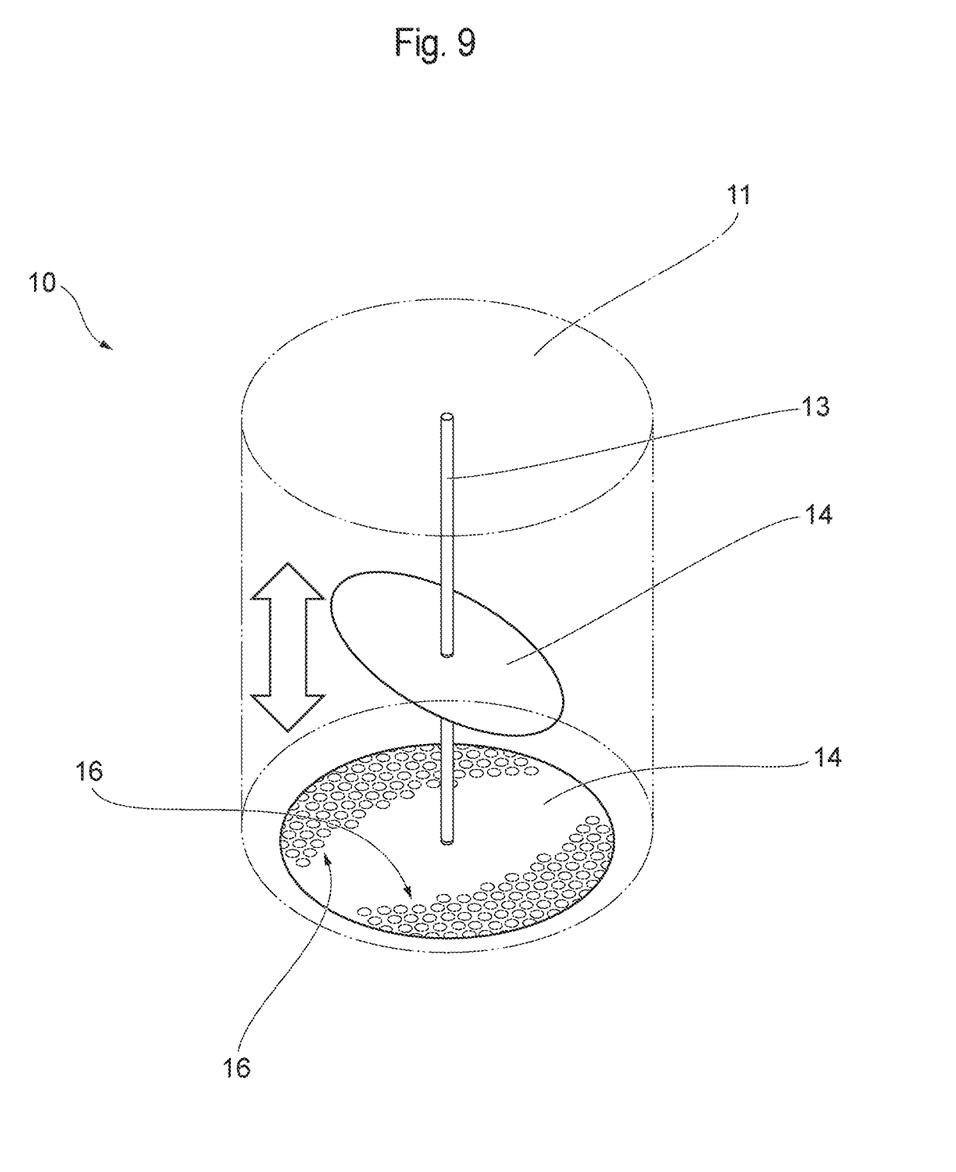
FIG. 9 schematically shows a configuration example of a bioreactor provided with stirring blades in multiple stages.

The bioreactor 10 according to the present embodiment includes: a culture tank 11, a seal 12, a driving shaft (stirring shaft) 13, and a stirring blade 14, as shown in FIG. 1. The conditions under which the driving shaft 13 and the like are placed in the culture tank 11 may include, as shown in FIG. 2, a bottom attachment where the driving shaft 13 is attached to a bottom part of the culture tank 11 and a side attachment where the driving shaft 13 is attached to a side part of the culture tank 11. The culture tank 11 has a three-dimensional body part having a shape obtained by extending a circular or rectangle planar shape in the longitudinal direction. The seal 12 is formed of a film member made of a flexible material, such as rubber, which follows the movement of the driving shaft 13, or a bellows structure made of a material such as a metal or Teflon®, and covers an upper opening of the culture tank 11 to be airtight. The driving shaft 13 is linked, at the upper part thereof, to a vertical motion device, for example, a reciprocating motion motor 15, penetrates the seal 12 at the middle part thereof, and is airtightly fixed to the seal 12. The stirring blade 14 has a planar shape or a folded structure, and the planer shape is, for example, as shown in FIG. 3, an oval shape (FIG. 3(B)), a rectangle (FIG. 3(C)), or a through hole structure (FIG. 3(D)) obtained by providing a circular plate with a through hole 16, each of which is obtained by reducing an area of a circular shape (FIG. 3(A)) orthogonally. A stirring blade 14 in one or more stages is fixed to the driving shaft 13. When the stirring blade 14 has a through hole 16, a shearing action on a fluid or cells passing through the through hole 16 can be increased (see FIG. 9). The through hole 16 may be constituted by a large hole provided in the stirring blade 14 (FIG. 3(D)) or a plurality of small holes provided in a predetermined area of the stirring blade 14 (FIG. 9).

The stirring blade 14 may be stirring blades in multiple stages. For example, the bioreactor 10 shown in FIG. 9 has a two-stage blade configuration including: a stirring blade 14 on an upper stage, attached to the driving shaft 13; and a stirring blade 14 on a lower stage, provided with through holes 16, and in particular, a shearing effect on the stirring blade 14 on the lower stage is further improved.

In the bioreactor 10 in the present embodiment, the stirring blade attached to the driving shaft (stirring shaft) 13 perpendicularly may be caused to perform forward and reverse rotation while controlling with a servomotor. Moreover, the control of the forward and reverse rotation by this servomotor is controlled by a driver, so that a forward and reverse motion motor 15 is configured. Thus, the forward and reverse rotation (the acceleration, the wave profile, and the speed) can be controlled by the servomotor.

The bioreactor 10 provides a physicochemical environment favorable for optimum cell growth, cell metabolism, differentiated maturity of megakaryocyte cells, multinucleation of megakaryocyte cells, formation of proplatelets, production of platelets, and maintenance of bioactivity of platelets. The bioreactor 10 may include an aerator, an air exhauster, a temperature adjuster, a pH controller, a dissolved oxygen tension (DOT) adjuster, a baffle, a sparger, and a port.

The shape of the culture tank 11 in the bioreactor 10 is not limited to particular shapes. The culture tank 11 may have, for example, a vertically-long, tubular shape and have a flat surface at each of the top and the bottom.

The volume of the culture tank is at least 300 mL, preferably at least 1 L, 50 L, more preferably at least 200 L, more preferably at least 500 L, yet more preferably at least 1000 L, and yet more preferably at least 2000 L.

In the present specification, "megakaryocyte cells" are the largest cells that reside in the bone marrow in vivo and are characterized by releasing platelets. The megakaryocyte cells are characterized by being cell surface marker CD41a-, CD42a-, and CD42b-positive and further express a marker selected from the group consisting of CD9, CD61, CD62p, CD42c, CD42d, CD49f, CD51, CD110, CD123, CD131, and CD203c in some cases. The multinucleated (polyploidizated) "megakaryocyte cells" have genomes that are 16 to 32 times those in the general cells. However, when the "megakaryocyte cells" merely mentioned in the present specification include multinucleated megakaryocyte cells and megakaryocyte cells before multinucleation as long as including the above-described characteristics. The "megakaryocyte cells before multinucleation" means the same as "immature megakaryocyte cells" or "megakaryocyte cells in the growth state".

The megakaryocyte cells can be obtained by various known methods. A non-limiting example of a method for producing megakaryocyte cells can be the method described in WO 2011/034073. In the method, cancer genes and Polycomb genes in the "cells before being differentiated into megakaryocyte cells" are subjected to forced expression, so that infinitely growing, immortalized megakaryocyte cell strain can be obtained. The immortalized megakaryocyte cells can be obtained also by subjecting an apoptosis inhibitory gene in the "cells before being differentiated into megakaryocyte cells" to forced expression in accordance with the method described in WO 2012/157586. The multinucleation of these immortalized megakaryocyte cells is progressed by cancellation of forced expressions of the genes, thereby releasing platelets.

To obtain megakaryocyte cells, the methods described in the above documents can be combined. In this case, forced expressions of cancer genes, Polycomb genes, and apoptosis inhibitory genes can be performed in parallel or in sequence. For example, cancer genes and Polycomb genes are subjected to forced expression, the forced expression is inhibited, apoptosis inhibitory genes are subsequently subjected to forced expression, and the forced expression is inhibited, to obtain multinucleated megakaryocyte cells. The multinucleated megakaryocyte cells can be obtained also by subjecting cancer genes, Polycomb genes, and apoptosis inhibitory genes to forced expression in parallel. The multinucleated megakaryocyte cells can be obtained also by subjecting cancer genes and Polycomb genes to forced expression, subsequently subjecting apoptosis inhibitory genes to forced expression, and inhibiting the forced expressions in parallel.

In the present specification, "cells before being differentiated into megakaryocyte cells" are cells having a differentiation potential to megakaryocyte and means cells in various differentiation stages from hematopoietic stem cell system to megakaryocyte cells. Non-limiting examples of cells before being differentiated into megakaryocyte include hematopoietic stem cells, hematopoietic progenitor cells, CD34-positive cells, and megakaryocyte-erythroid progenitor cells (MEP). These cells can be obtained by isolating from, for example, bone marrow, umbilical cord blood, and peripheral blood or by inducing differentiation of pluripotent stem cells such as ES cells, iPS cells that further undifferentiated cells.

In the present specification, "cancer genes" are genes that induce canceration of cells in in vivo, and examples thereof include MYC family genes (for example, c-MYC, N-MYC, L-MYC), SRC family genes, RAS family genes, RAF family genes, and protein kinase family genes such as c-Kit, PDGFR, and Abl.

In the present specification, "Polycomb genes" are known as genes that function to negatively regulate CDKN2a (INK4a/ARF) genes and avoid cellular senescence (Ogura et al., Regenerative Medicine, vol. 6, No. 4, pp. 26-32; Jseus et al., Jseus et al., Nature Reviews Molecular Cell Biology vol. 7, pp. 667-677, 2006; Proc. Natl. Acad. Sci. USA vol. 100, pp. 211-216, 2003). Non-limiting examples of the Polycomb genes include BMI1, Mel18, Ring1a/b, Phc1/2/3, Cbx2/4/6/7/8, Ezh2, Eed, Suz12, HADC, and Dnmt1/3a/3b.

In the present specification, "apoptosis inhibitory gene" is a gene having a function of inhibiting apoptosis of cells, and examples thereof include a BCL2 gene, a BCL-xL gene, a Survivin gene, and a MCL1 gene.

The forced expressions of the genes and the cancellation of the forced expressions can be performed by the methods described in WO 2011/034073, WO 2012/157586, WO 2014/123242, and Nakamura S et al, Cell Stem Cell. 14, 535-548, 2014, other known methods, or equivalent methods thereto.

In the present specification, "platelets" are one of cell components in blood and are characterized by being CD41a positive and CD42b positive. Platelets play an important role in thrombus formation and hemostasis, and are involved in pathophysiology of tissue regeneration and inflammation after injury. When platelets are activated by bleeding, cytoadhesion receptors such as Integrin αIIBβ3 (glycoprotein IIb/IIIa, a complex of CD41a and CD61) are expressed on the membranes. Then, platelets are aggregated, and fibrin is coagulated by various blood coagulation factors released from platelets. Thus, thrombi are formed, and hemostasis is progressed.

The function of platelets can be evaluated through measurements by known methods. For example, the amount of activated platelets can be measured using antibodies to PAC-1 that specifically binds to Integrin αIIBβ3 on the activated platelet membranes. Alternatively, the amount of activated platelets may be measured by detecting CD62P (P-selectin) that is an activation marker of platelets with an antibody. For example, the measurement can be performed by gating platelets with an antibody to an activation independent platelet marker CD61 or CD41 and thereafter detecting binding of an anti-PAC-1 antibody and an anti-CD62P antibody, using flow cytometry. These steps can be performed in the presence of adenosine diphosphate (ADP).

The function of platelets can be evaluated by checking whether the platelets bind to fibrinogen in the presence of ADP. When platelets bind to fibrinogen, integrin that is required at the beginning of thrombus formation is activated.

Figure 6:
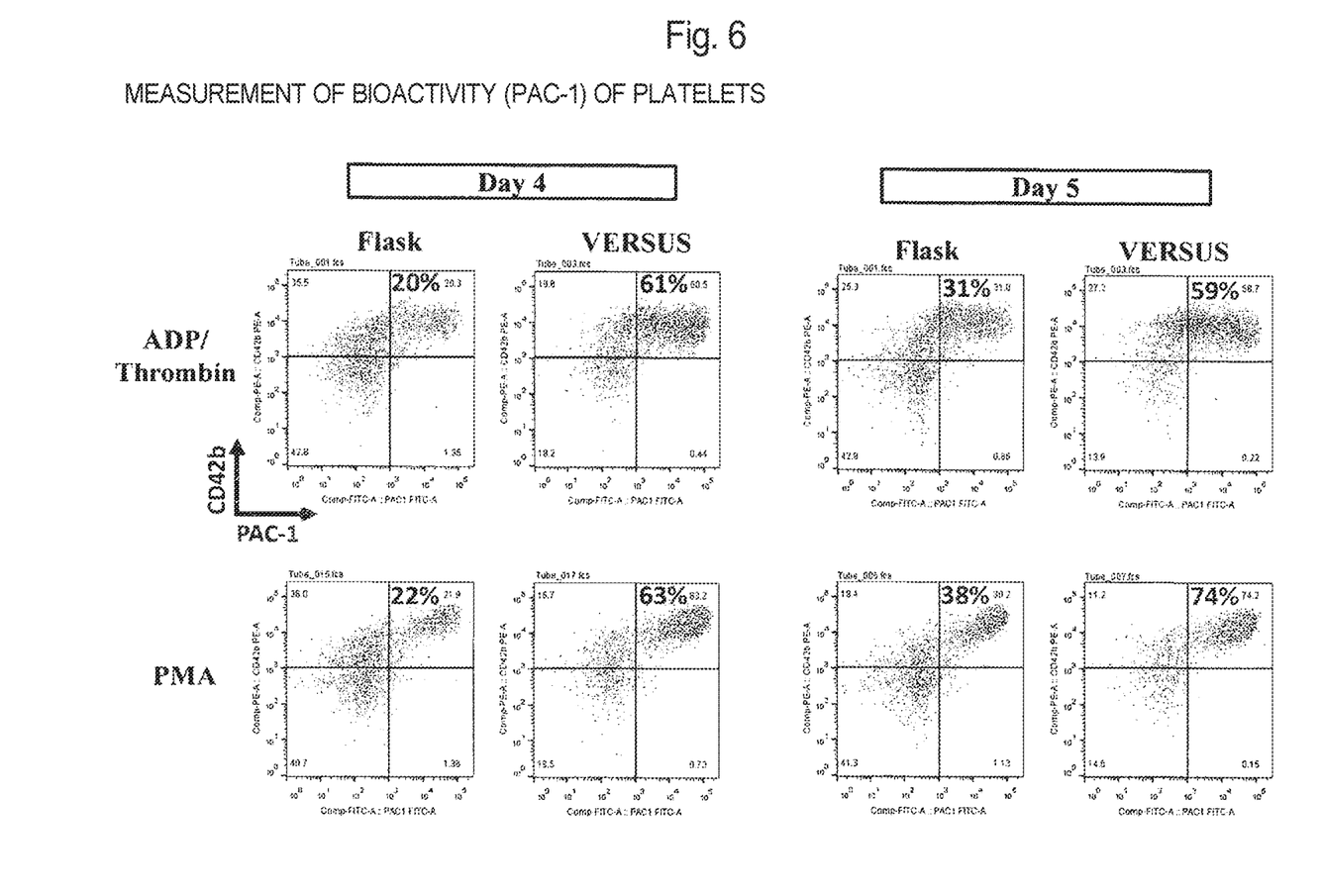
FIG. 6 shows the results obtained by subjecting platelets obtained by stirring culture or shaking culture of megakaryocyte cells to flow cytometry before or after stimulation with PMA or ADP using an anti-CD42b antibody and an anti-PAC-1 antibody.

The function of platelets can be evaluated also by a method for visualizing and observing a thrombus formation ability in vivo as shown in FIG. 6 of WO 2011/034073.

When platelets have a low expression rate of CD42b or a low annexin V positive rate, the platelets are evaluated as being degraded or abnormal. These platelets do not have a sufficient thrombus formation function and a sufficient hemostasis function and thus are not clinically useful.

In the present specification, "degradation of platelets" refers to a reduction in CD42b (GPIbα) on platelet membranes. Thus, degraded platelets contain platelets having a reduced expression level of CD42b and platelets where extracellular domains of CD42b are cleaved by a shedding reaction. When CD42b is not present on platelet membranes, the platelets cannot coassemble with a von Willebrand factor (VWF), and the blood coagulation function of the platelets is thus lost. The degradation of platelets can be evaluated using a CD42b negative rate (or the number of CD42b negative particles) to the CD42b positive rate (or the number of CD42b positive particles) in fractions of platelets as an indicator. The higher the CD42b negative rate to the CD42b positive rate is, or the higher the number of CD42b negative particles to the number of CD42b positive particles is, the platelets are more degraded. The CD42b positive rate means a proportion of platelets that can bind to an anti-CD42b antibody in the platelets contained in fractions of platelets, and the CD42b negative rate means the proportion of platelets to which an anti-CD42b antibody does not bind in the platelets contained in fractions of platelets.

In the present specification, "abnormal platelets" are platelets where phosphatidylserine that is negatively-charged phospholipid is exposed from the inside of a lipid bilayer to the outside. It is known that phosphatidylserine is exposed to platelet membranes in vivo with activation of platelets, and many blood coagulation factors are bound to the phosphatidylserine, and thus a blood coagulation cascade reaction is amplified. In abnormal platelets, much phosphatidylserine is always exposed to abnormal platelet membranes, and when the abnormal platelets are administered to a subject, an excessive blood coagulation reaction may be caused, which results in a serious pathological condition such as disseminated intravascular coagulation. Annexin V is bound to phosphatidylserine, and thus, phosphatidylserine on the platelet membranes can be detected by a flow cytometer using a binding amount of fluorescence-labeled annexin V as an indicator. Thus, the amount of abnormal platelets can be evaluated by the annexin V positive rate, i.e., the proportion of the number of platelets to which annexin is bound in fractions of platelets. The higher the annexin V positive rate is, or the higher the number of annexin V particles is, the higher the amount of abnormal platelets is.

The culture conditions of megakaryocyte cells in the present invention can be normal conditions. For example, the temperature can be about 35° C. to about 42° C., about 36° C. to about 40° C., or about 37° C. to about 39° C. at 5% to 15% $CO_2$ and/or 20% $O_2$.

A medium to be used in culturing of megakaryocyte cells is not limited to particular media, and any of known media that are favorable for producing platelets from megakaryocyte cells and media equivalent thereto can be used as appropriate. For example, a medium used to culture animal cells can be prepared as a basal medium. Examples of the basal medium include an IMDM, a Medium 199, an Eagle's Minimum Essential Medium (EMEM), an αMEM, a Dulbecco's modified Eagle's Medium (DMEM), a Ham's F12 medium, a RPMI 1640 medium, a Fischer's medium, and a Neurobasal Medium (Life Technologies Corporation), and mixtures thereof.

The medium may contain a serum or plasma or is serum-free. If necessary, the medium may contain at least one substance selected from, for example, albumin, insulin, transferrin, selenium, fatty acid, trace elements, 2-mercaptoethanol, thiol glycerol, monothioglycerol (MTG), lipid, amino acids (for example, L-glutamine), ascorbic acid, heparin, nonessential amino acids, vitamins, growth factors, low molecular weight compounds, antibiotics, anti-oxidizing agents, pyruvic acid, buffer agents, inorganic salts, and cytokine. Cytokine is a protein that accelerates hematopoietic differentiation, and examples thereof include vascular endothelial growth factor (VEGF), thrombopoietin (TPO), various TPO-like active substances, Stem Cell Factor (SCF), an ITS (insulin-transferrin-selenite) supplement, and an ADAM inhibitor. A preferred medium in the present invention is an IMDM medium containing serum, insulin, transferrin, serine, thiol glycerol, ascorbic acid, and TPO. The medium may further contain SCF and may further contain heparin. The concentration of each component is not limited to particular concentrations, and for example, the concentration of TPO can be about 10 ng/mL to about 200 ng/mL, or about 50 ng/mL to about 100 ng/mL, the concentration of SCF can be about 10 ng/mL to about 200 ng/mL or about 50 ng/mL, and the concentration of heparin can be about 10 U/mL to about 100 U/mL or about 25 U/mL. Phorbol ester (for example, phorbol-12-myristate-13-acetate; PMA) may further be added to the medium.

When a serum is used, a human serum is desirable. For example, a human plasma may be used as a substitute for the serum. By the method according to the present invention, platelets that are comparable to those obtained using a serum can be obtained even using these components.

When a drug-responsive gene expression induction system such as a Tet-On® or a Tet-Off® system is used for forced expression of genes or cancellation of the force expression, a suitable drug such as tetracycline or doxycycline may be caused to be contained in a medium in the step of the forced expression, and the forced expression may be inhibited by removing the suitable drug from the medium.

The step of culturing megakaryocyte cells in the present invention is conducted by suspension culture and thus can be conducted without feeder cells.

The present invention encompasses platelets produced by the method according to the present invention.

A method for producing a platelet preparation according to the present invention includes: the step of culturing megakaryocyte cells by the method according to the present invention to produce platelets and collecting a fraction in which platelets are abundant from a culture; and the step of removing a hematopoietic cell component other than platelets from the fraction. The step of removing a hematopoietic cell component can be conducted by removing a hematopoietic cell component other than platelets that contain megakaryocyte cells using a leukocyte removal filter (for example, manufactured by Terumo corporation or Asahi Kasei Medical Co., Ltd.). A further specific method for producing a platelet preparation is described in, for example, WO 2011/034073.

The method for producing a blood preparation according to the present invention includes: the step of producing a platelet preparation by the method according to the present invention; and the step of mixing the platelet preparation and another component. Another component can be, for example, an erythroid cell.

Other components that contribute to stabilization of cells can further be added to the platelet preparation and the blood preparation.

The disclosure of all of the patent document and the non-patent document cited in the present specification are incorporated in the present specification by reference.

Example 1

The following describes the present invention in detail on the basis of the examples. The present invention, however, is by no means limited thereto. Those skilled in the art can change the present invention in various embodiments without departing from the meaning of the present invention, such changes are also included in the scope of the present invention.

1. Production of Immortalized Megakaryocyte Cells

1-1. Preparation of Hematopoietic Progenitor Cells from iPS Cells

A differentiation culture from human iPS cells (TKDN SeV2: iPS cells derived from human fetal skin fibroblast, established using Sendai virus) to blood cells was conducted in accordance with the method described in Takayama N., et al., J Exp Med. 2817-2830 (2010). That is, human ES/iPS cell colonies were co-cultured with C3H10T1/2 feeder cells in the presence of 20 ng/mL VEGF (R&D Systems, Inc.) for 14 days to produce hematopoietic progenitor cells (HPC). The co-culture was conducted under culture conditions at 20% $O_2$ and 5% $CO_2$ (hereinafter the same, unless otherwise specifically described).

1-2. Gene Delivery System

As a gene delivery system, a lentiviral vector system was used. A lentiviral vector is a Tetracycline-controlled Tet-On (registered trademark) gene expression induction system vector. Lentiviral vectors were produced by replacing the mOKS cassette of LV-TRE-mOKS-Ubc-tTA-I2G (Kobayashi, T., et al., Cell 142, 787-799 (2010)) with c-MYC, BMI1, and BCL-xL. The lentiviral vectors were LV-TRE-c-Myc-Ubc-tTA-I2G, LV-TRE-BMI1-Ubc-tTA-I2G, and LV-TRE-BCL-xL-Ubc-tTA-I2G.

Virus particles were produce by gene transfer of the lentiviral vectors into 293T cells using any method.

Genes of BMI1, MYC, and BCL-xL are transferred to genomic sequences of target cells by infecting various particles with the target cells. These genes stably transferred to the genomic sequences can be subjected to forced expression by adding doxycycline to a medium (#631311, Clontech Laboratories, Inc.).

1-3. Infection of c-MYC and BMI1 Virus to Hematopoietic Progenitor Cells

On 6 well plates to which C3H10T1/2 feeder cells were seeded in advance, $5 \times 10^4$ cells/well HPC obtained by the above-described method was seeded, and c-MYC and BMI1 were subjected to forced expression by the lentivirus method. In this case, 6 wells were used per one kind of cell strain. That is, virus particles were added to a medium to be a MOI of 20. The cells were infected with the various particles by spin infection (centrifugation at 32° C. and 900 rpm for 60 minutes). This operation was performed a total of two times every 12 hours.

As the medium, a medium obtained by further adding protamine to a medium (hereinafter referred to as a differentiation medium) that is obtained by adding 50 ng/mL Human thrombopoietin (TPO) (R&D Systems, Inc.), 50 ng/mL Human Stem Cell Factor (SCF) (R&D Systems, Inc.), and 2 μg/mL Doxycycline (Dox) to a basal medium (IMDM (Iscove's Modified Dulbecco's Medium) (Sigma-Aldrich) containing 15% Fetal Bovine Serum (GIBCO), 1% Penicillin-Streptomycin-Glutamine (GIBCO), 1% Insulin, Transferrin, Selenium Solution (ITS-G) (GIBCO), 0.45 mM 1-Thioglycerol (Sigma-Aldrich), and 50 μg/mL L-Ascorbic Acid (Sigma-Aldrich)), to have a final concentration of 10 μg/mL.

1-4. Production and Maintenance Culture of Megakaryocyte Self-Growth Strain

Assuming that the day on which the infection with cMYC and BMI1 virus were performed by the above-described method was day 0 of infection, megakaryocyte self-growth strains were produced by culturing cMYC gene transfer-type megakaryocyte cells and BMI1 gene transfer-type megakaryocyte cells. The forced expression of the BMI1 gene and the c-MYC gene was performed by adding 1 μg/mL doxycycline (#631311, Clontech Laboratories, Inc.) to a medium.

Day 2 to Day 11 of Infection

Blood cells infected with the virus by the above-described method were collected by pipetting, centrifuged at 1200 rpm for 5 minutes to remove supernatant, thereafter suspended in a new differentiation medium, and seeded on new C3H10T1/2 feeder cells (6 well plates). On day 9 of infection, the same operation was performed to subculture. The cell number was counted, and the cells were seeded on C3H10T1/2 feeder cells at $1 \times 10^5$ cells/2 mL/well (6 well plates).

Day 12 to Day 13 of Infection

The same operation as performed on day 2 of infection was performed. The cell number was counted, and the cells were seeded on C3H10T1/2 feeder cells at $3 \times 10^5$ cells/10 mL/100 mm-dish (100 mm dish).

Day 14 of Infection

Blood cells infected with virus were collected, and an antibody reaction was performed using 2 μL of anti-human CD41a-APC antibody (BioLegend, Inc.), 1 μL of anti-human CD42b-PE antibody (eBioscience, Inc.), and 1 μL of anti-human CD235ab-pacific blue (BioLegend, Inc.) antibody per $1.0 \times 10^5$ cells. After the antibody reaction, analysis was performed using FACS Verse (BD). Cells having the CD41a positive rate of 50% or more on day 14 of infection were regarded as megakaryocyte self-growth strains.

1-5. Infection of Megakaryocyte Self-Growth Strains with BCL-xL Virus

BCL-xL was transferred to the megakaryocyte self-growth strains on day 14 of infection by the lentivirus method. Virus particles were added to a medium to be a MOI of 10. The cells were infected with the BCL-xL virus by spin infection (centrifugation at 32° C. and 900 rpm for 60 minutes). The forced expression of the BCL-xL gene was performed by 1 μg/mL doxycycline (#631311, Clontech Laboratories, Inc.) to the medium.

1-6. Production and Maintenance Culture o Immortalized Megakaryocyte

Day 14 to Day 18 of Infection

Megakaryocyte self-growth strains to which BCL-xL was transferred, obtained by the above-described method were collected and centrifuged at 1200 rpm for 5 minutes. After the centrifugation, precipitated cells were suspended in a new differentiation medium and thereafter seeded on C3H10T1/2 feeder cells at $2 \times 10^5$ cells/2 mL/well (6 well plates).

Day 18 of Infection: Subculture

The cell number was counted, and the cells were seeded at $3 \times 10^5$ cells/10 mL/100 mm-dish.

Day 24 of Infection: Subculture

The cell number was counted, and the cells were seeded at $1 \times 10^5$ cells/10 mL/100 mm-dish. Thereafter, subculture was performed every 4 to 7 days for maintenance culture.

Megakaryocyte self-growth strains to which BCL-xL was transferred were collected on day 24 of infection, and immunostaining was performed using 2 μL of anti-human CD41a-APC antibody (BioLegend, Inc.), 1 μL of anti-human CD42b-PE antibody (eBioscience, Inc.), and 1 μL of anti-human CD235ab-pacific blue (Anti-CD235ab-PB, BioLegend, Inc.) antibody per $1.0 \times 10^5$ cells. After the immunostaining, analysis was performed using FACS Verse (BD). Cells having the CD41a positive rate of 50% or more on day 24 of infection were regarded as immortalized megakaryocyte cell strains. The cells that could be grown for 24 days or more after infection were determined as an immortalized megakaryocyte cell strain SeV2-M KCL.

The obtained SeV2-MKCL was subjected to static culture in 10 cm-dish (10 mL/dish). As a medium, a medium obtained by adding, to an IMDM as a basal medium, the following components (the concentrations are final concentrations).

FBS (#172012, lot.12E261, Sigma), 15%
L-Glutamin (#25030-081, Gibco), 2 mM
ITS (#41400-045, Gibco), 100-folded
MTG (monothioglycerol, #M6145-25ML, Sigma) 450 μM
Ascorbic acid (#A4544, Sigma) 50 μg/mL
Puromycin (#P8833-100MG, Sigma) 2 μg/mL
SCF (#193-15513, Wako Pure Chemical Industries Ltd.) 50 ng/mL
TPO-like action substance, 200 ng/mL
Culture conditions were 37° C. and 5% of $CO_2$ 2. Generation of Platelets Subsequently, the forced expression was cancelled by culturing the SeV2-MKCL in a medium containing no doxycycline. Specifically, the immortalized megakaryocyte cell strain (SeV2-MKCL) obtained in the method of the item 1 above was washed with PBS (−) twice and was suspended in the following medium at a seeding density of $1.0 \times 10^5$ cells/mL.

The medium is obtained by adding the following components to IMDM (the concentrations are final concentrations).

Figure 4:
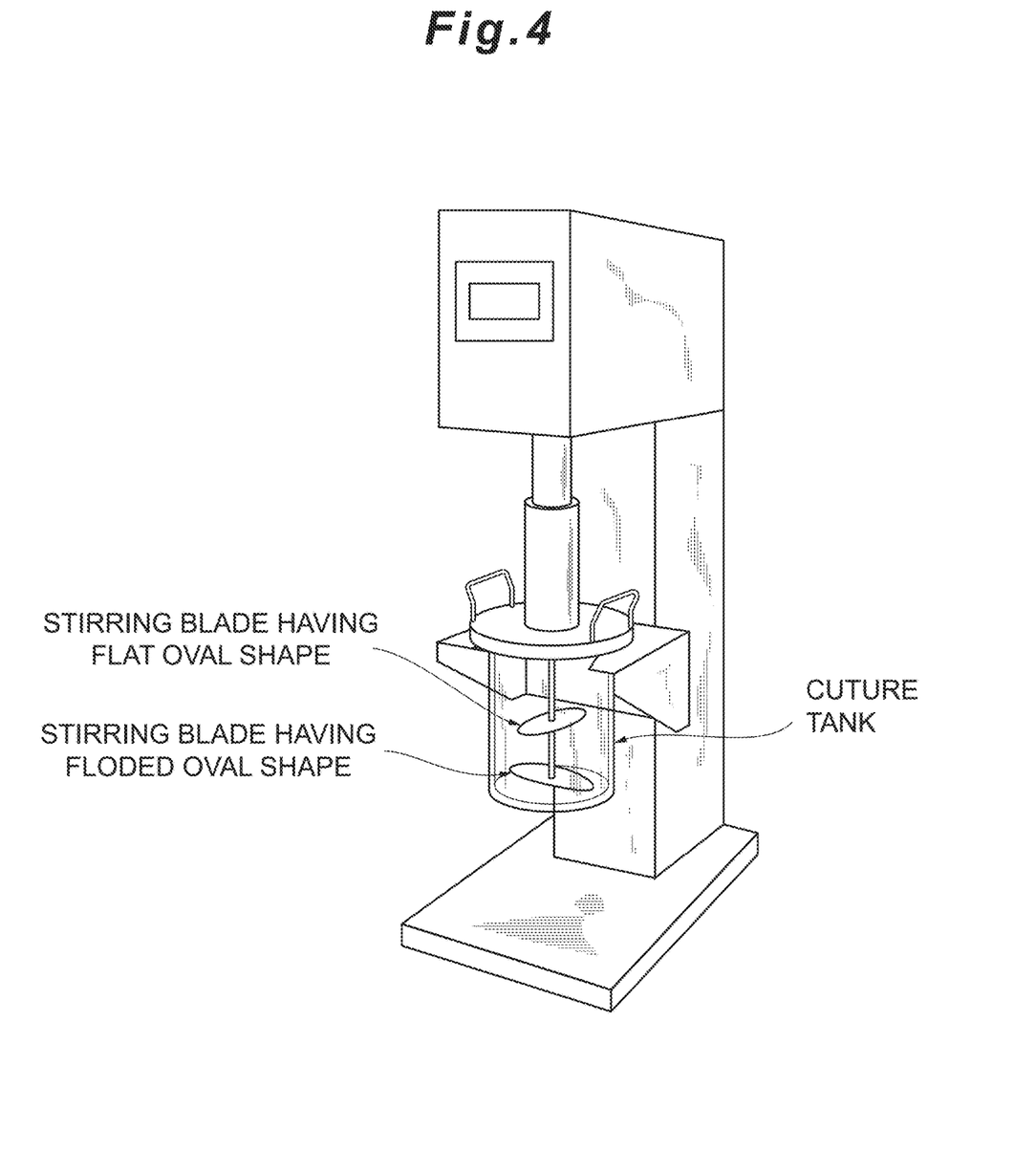
FIG. 4 shows a structure of VMF culturing device used in the example of the present invention.

FBS, 15%
L-Glutamine (#25030-081, Gibco), 2 mM
ITS (#41400-045, Gibco), 100-folded
MTG (monothioglycerol, #M6145-25ML, Sigma), 450 μM
ascorbic acid (#A4544, Sigma), 50 μg/mL
SCF (#193-15513, Wako Pure Chemical Industries Ltd.), 50 ng/mL
TPO-like active substance, 200 ng/mL
ADAM inhibitor, 15 μM
SR1, 750 nM
ROCK inhibitor, 10 μM The immortalized megakaryocyte cell strain (SeV2-MKCL) obtained by the method of the item 1 above was suspended in the medium to prepare a cell suspension. To a bioreactor 10, 2.4 L or the cell suspension was added, and to a 125 mL-shaker flask, 25 mL of the cell suspension was added. The bioreactor 10 has a stirring blade 14 in one or more stages, and a 3.0 L-VMF culturing device (hereinafter referred to as VMF) that can reciprocally move the stirring blade 14 in the vertical direction was used. Specifications of VMF are as follows. The outer body dimensions (mm): 300 W×485 D×890 H; the dimensions of the culture tank 11 (mm): 140 (inner diameter)×203 (depth); the liquid amount of the culture tank 11: 3.0 L; the stirring blade 14: folded oval shape structure (lower stage)+flat oval shape (upper stage), two-stage attachment; the direct driven type: linear shaft driven non-seal type; temperature adjustment range: room temperature +5° C. to 20° C.; range of vertical oscillation: 10 mm to 30 mm, maximum blade speed in vertical movement: 80 mm/s to 150 mm/s; measurement control: stirring, the temperature, the pH, dissolved oxygen, level, field. FIG. 4 shows the VMF.

In the VMF, 2.4 L of the suspension of the immortalized megakaryocyte cell strain was cultured. The culturing environment was 37° C. and 5% $CO_2$. The stirring speed was 1.6 Hz, and the stirring stroke length was 3 cm.

In a 125 mL-shaker flask, 25 mL of the suspension of the immortalized megakaryocyte cell strain was cultured. The shaking culture was performed using a shaking incubator (AniCell, N-BIOTEK Inc.) at 37° C., 5% $CO_2$, and 100 rpm.

3. Measurement of Platelets

To subject platelets produced in the method of the item 2 above to measurement, a cultured supernatant sample was collected after 6 days of the culture and were stained and analyzed using flow cytometry. The number of CD41a positive, CD42b positive particles was determined as the number of normal platelets, the number of CD41a positive, CD42b negative particles was determined as the number of degraded platelets. The number of annexin V-positive particles was determined as the number of abnormal platelets. Moreover, the sample was stimulated with PMA or ADP/Thrombin, and the PAC-1 positive rate and the CD62p positive rate before after the stimulation were calculated to measure bioactivity.

Specific measurement methods are as follows.

3-1. Measurement of Platelets

To measure bioactivity of each of the normal platelets, degraded platelets, and the platelets, 900 mL of diluent was added to each 1.5 mL-microtube, and 100 mL of a culture supernatant was then further added thereto, they were mixed. To each FACS tube, 200 mL of diluted, mixed culture supernatant was dispensed, and the following labeled antibody or protein was further added to stain. To subject the abnormal platelets to measurement, 100 mL of the culture supernatant was dispensed to each FACS tube, and the following labeled antibody or protein was further added to stain, and the mixture was diluted 5-fold with an annexin V binding buffer (BD) immediately before the analysis using flow cytometer, and then the analysis was conducted.

The antibodies used are as follows.

Measurement of Normal Platelets and Degraded Platelets
0.5 μL anti-CD41 antibody, labeled with APC (303710, BioLegend, Inc.)
0.5 μL anti-CD42a antibody, labeled with PB (48-0428-42, eBioscience, Inc.)
0.5 μL anti-CD42b antibody, labeled with PE (12-0428-42, eBioscience, Inc.)

Measurement of Bioactivity of Platelets
0.5 μL anti-CD42a antibody, labeled with PB (48-0428-42, eBioscience, Inc.)
0.5 μL anti-CD42b antibody, labeled with PE (12-0428-42, eBioscience, Inc.)
0.5 μL anti-CD62p antibody, labeled with APC (304910, BioLegend, Inc.)
10 μL anti-PAC-1 antibody, labeled with FITC (303704, BD)

Measurement of the Number of Abnormal Platelets
0.5 μL anti-CD41 antibody, labeled with APC (303710, BioLegend, Inc.)
0.5 μL anti-CD42a antibody, labeled with PB (48-0428-42, eBioscience, Inc.)
5 (L, labeled with Annexin V FITC (556419, BD)

3-2. Measurement of the Amount of Produced Normal Platelets

Figure 5:
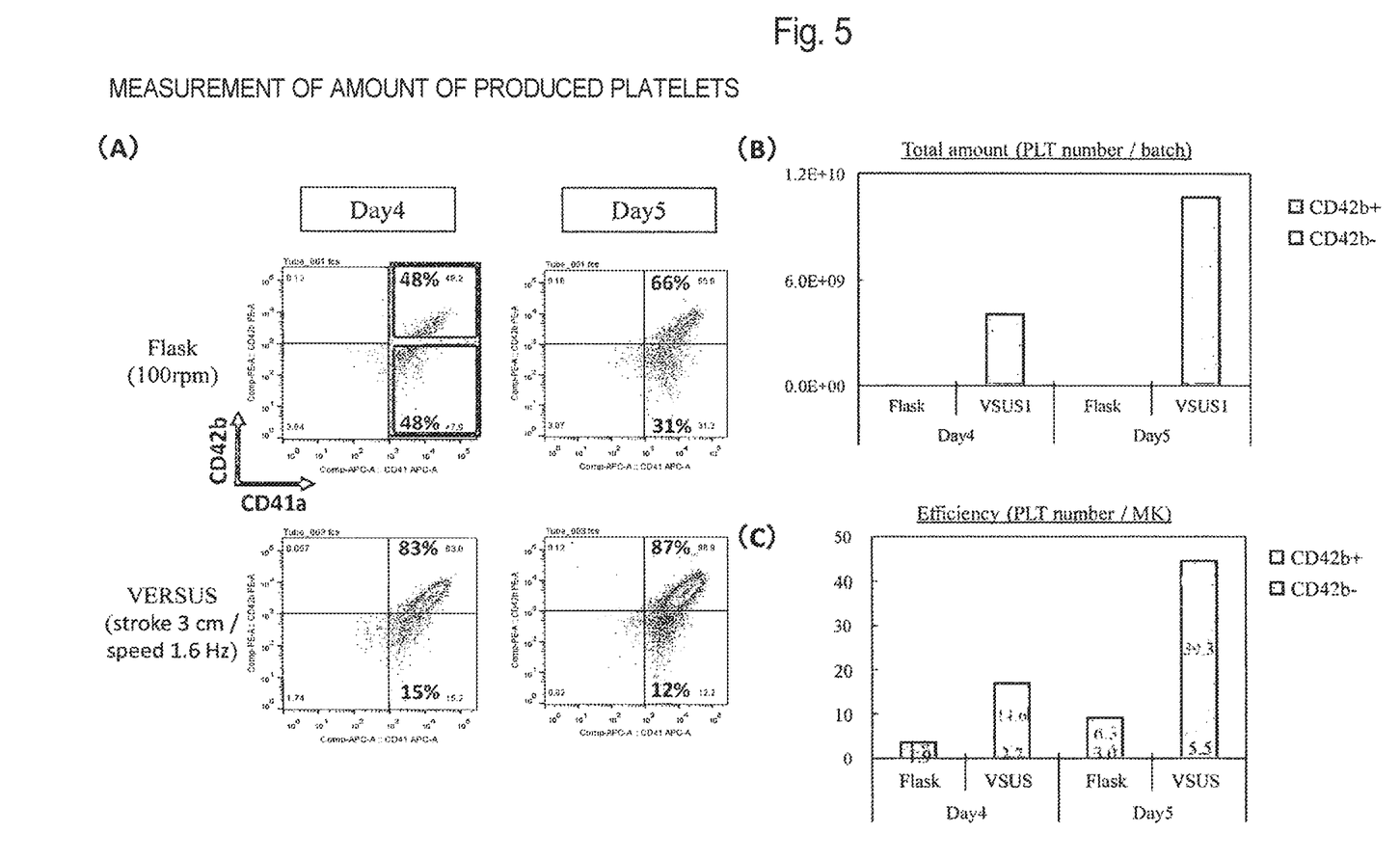
FIG. 5 shows results obtained by subjecting platelets obtained by stirring culture or shaking culture of megakaryocyte cells to flow cytometry using an anti-CD42b antibody and an anti-CD41a antibody.

FIG. 5 shows the results. The amount of produced normal platelets was higher in culturing in the VMF, compared with that in culturing using a shaker flask (FIG. 5(B)). When the number of normal platelets per the number of megakaryocyte cells is calculated as production efficiency of the normal platelets, the production efficiency of the normal platelets was about 6.0 to 7.7 times higher in the culturing in the VMF than that in the culturing using a shaker flask (FIG. 5(C)). That is, the number of produced normal platelets per the number of megakaryocyte cells could be increased by culturing in the VMF, compared with the conventional culturing using a shaker flask.

3-3. Measurement of Degraded Platelets

In the measurement of the degraded platelets, each treated sample was analyzed by the method of the item 3-1 above using a flow cytometer, and the number of CD41a-positive, CD42b positive particles, and the number of CD41a positive, CD42b negative particles were measured. Then, the number of CD41a-positive, CD42b positive particles was determined as the number of normal platelets, and the number of CD41a positive, CD42b negative particles was determined as the number of degraded platelets, and the ratio of the number of degraded platelets to the number of normal platelets was calculated.

FIG. 5 shows the results. The ratio of the number of degraded platelets to the number of normal platelets in culturing in the VMF was about 0.31 to 0.39 times lower than that in culturing using a shaker flask (FIG. 5(A)). That is, the amount of produced degraded platelets could be reduced in culturing in the VMF, compared with conventional culturing using a shaker flask.

3-3. Measurement of Platelets Bioactivity

The stimulation of the platelets was conducted using 0.2 mM PMA (Phorbol 12-myristate 13-acetate, #P1585-1 MG, Sigma) or 100 μM ADP (#A2754, Sigma) and 0.5 U/mL Thrombin (Sigma) at room temperature. A measurement was conducted using FACSverce manufactured by BD after 30 minutes from the stimulation. The PAC-1 positive rate and the CD62p positive rate in fractions of the CD42a positive platelets before and after the stimulation were measured and comparatively evaluated.

Figure 7:
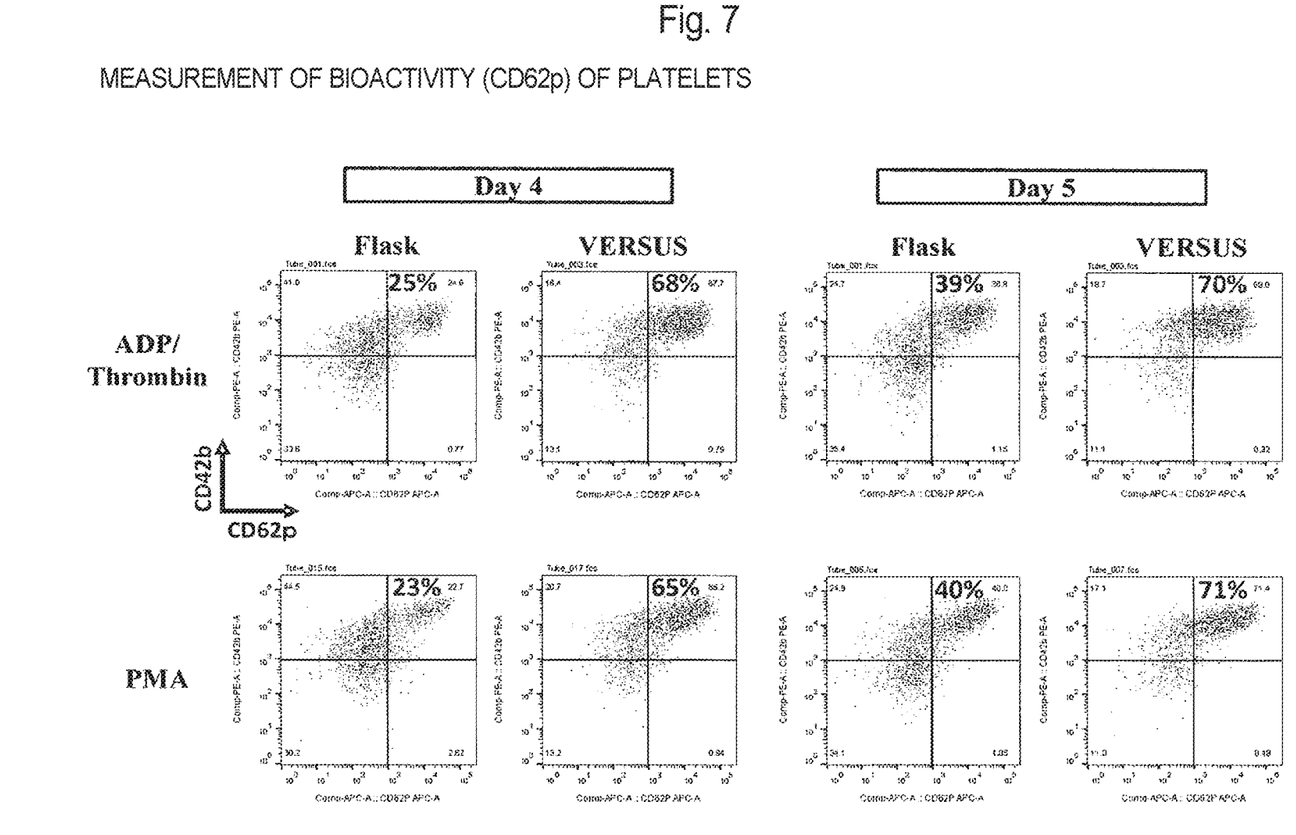
FIG. 7 shows the results obtained by subjecting platelets obtained by stirring culture or shaking culture of megakaryocyte cells to flow cytometry before or after stimulation with PMA or ADP using an anti-CD42b antibody and an anti-CD62p antibody.

FIGS. 6 and 7 show the results. The PAC-1 positive rate at the time of the stimulation with PMA or ADP/Thrombin was about 1.9 to 3.1 times higher in culturing in the VMF, compared with culturing using a shaker flask (FIG. 6). The CD62p positive rate was about 1.8 to 2.7 times or more higher in culturing in the VMF, compared with culturing using a shaker flask (FIG. 7). That is, the amount of produced platelets having high bioactivity could be increased by culturing in the VMF, compared with conventional culturing using a shaker flask.

3-4. Measurement of Abnormal Platelets

Each treated sample was analyzed by the method of the item 3-1 above using flow cytometer, and the number of annexin V-positive particles was measured. The number of CD42b positive, annexin V positive particles was determined as the number of abnormal platelets.

Figure 8:
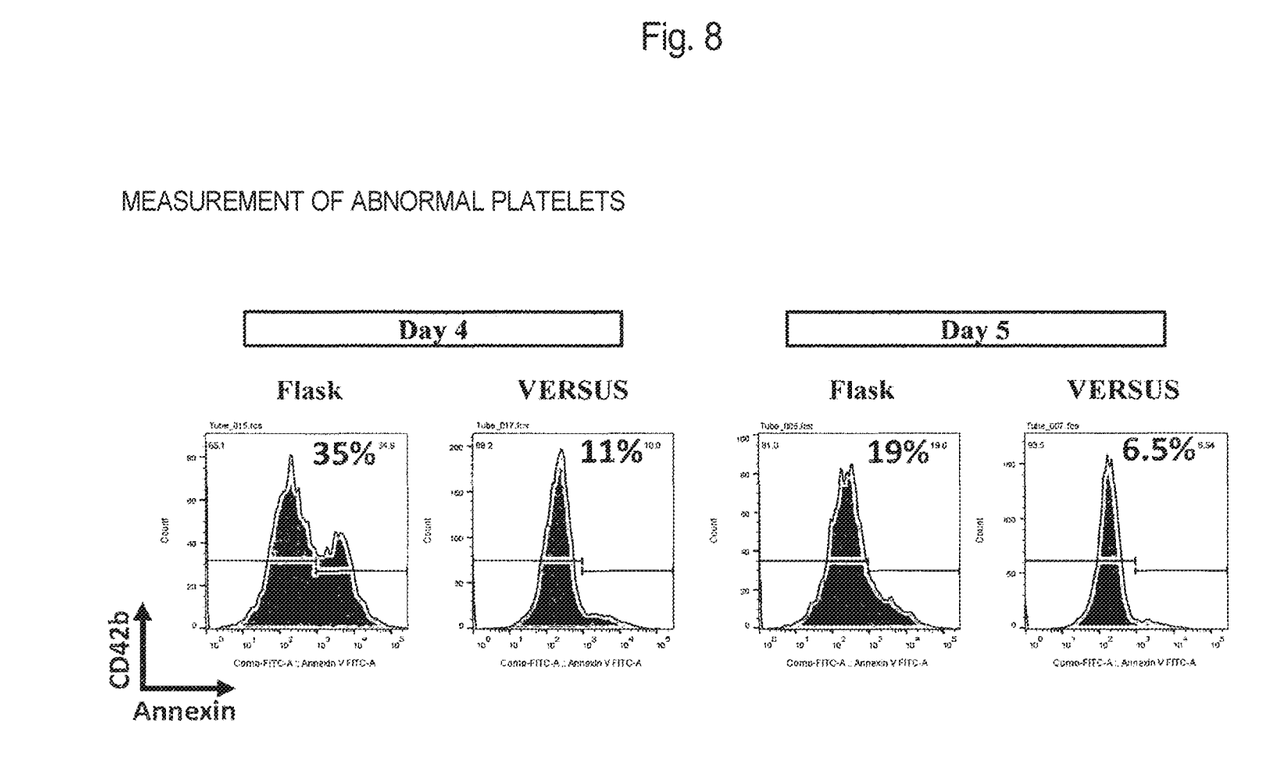
FIG. 8 shows the results obtained by measuring the annexin V binding rate in the platelets obtained by stirring culture or shaking culture of megakaryocyte cells, using flow cytometry.

FIG. 8 shows the results. The number of CD42b positive, annexin V positive particles was about 0.31 to less than 0.34 times reduced in the culturing in the VMF, compared with culturing using a shaker flask (FIG. 8). That is, the amount of produced abnormal platelets could be reduced by culturing in the VMF, compared with conventional culturing using a shaker flask.

INDUSTRIAL APPLICABILITY

It is obvious that high-quality platelets that cannot be obtained by shaking culture using shaker flasks can be obtained by the present invention. The present invention therefore can contribute to production of an industrial-scale large amount of platelets.

What is claimed is:

1. A method for producing platelets, which comprises:
a culturing step of culturing megakaryocyte cells excluding microorganism in a culture solution in a culture vessel, wherein in the culturing step, the culture solution is unsteadily stirred with two or more stirring blades fixed to a stirring shaft directly linked to a motor, at least one stirring blade of the one or more stirring blades is attached not to be orthogonal to the stirring shaft, and at least another stirring blade of the two or more stirring blades has folded oval shape structure, the stirring blades being configured for to move reciprocally in a vertical direction, a horizontal direction, or a forward and reverse rotation direction,
wherein a main surface of the stirring blade encounters resistance when the culture solution is being stirred,
wherein the culture vessel is a closed bioreactor, and
wherein physical shear stress is applied to the megakaryocyte cells by a reciprocal motion of the two or more stirring blades with vertical oscillation within a range between about 30 mm and about 40 mm and maximum blade speed in vertical movement within a range between about 100 mm/s and about 200 mm/s so that the platelets production from the megakaryocyte cells is promoted with an unsteady motion caused by the reciprocal motion as an optimum motion to produce the platelets without shaking operation.

2. The method according to claim 1, wherein
in the culturing step, the culture solution is unsteadily stirred with stirring blades in multiple stages.

3. The method according to claim 2, wherein
one of the two or more stirring blades used in the culturing step is attached to be orthogonal to the stirring shaft.

4. The method according to claim 2, wherein
the stirring blade having the folded oval shape is attached to be orthogonal to the stirring shaft.

5. The method according to claim 1, wherein
the stirring blade having the folded oval shape is attached to a stirring shaft in at least one stage to be orthogonal to the at least one stirring blade,
the at least one stirring blade has a flat oval shape, and
a bioreactor that reciprocally moves the stirring blades vertically to stir the culture solution is used in the culturing step.

6. The method according to claim 5, wherein
the two or more stirring blades include a stirring blade having a through hole.

7. The method according to claim 1, wherein
the culture vessel is a closed bioreactor.

8. The method according to claim 7, wherein
the megakaryocyte cells are obtained by subjecting, to forced expression, at least one selected from the group consisting of cancer genes, Polycomb genes, and apoptosis inhibitory genes in cells before being differentiated into megakaryocyte cells, and then cancelling the forced expression.

9. The method according to claim 1, wherein one of the two of more stirring blades is attached to a stirring shaft that is attached to a bottom part of the culture vessel via a bottom attachment, and the stirring shaft is attached to a side part of the culture vessel via a side attachment.

10. The method according to claim 1, wherein one of the two or more stirring blades has a two-stage blade configuration including a stirring blade on an upper stage and a stirring blade on a lower stage.

11. The method according to claim 10, wherein the stirring blade on the upper stage is attached to a stirring shaft, and the stirring blade on the lower stage is provided with through holes.

12. The method according to claim 1, wherein the culture vessel is stand still, a support shaft that supports the stirring blade moves reciprocally in the direction in which the support shaft extends to move the stirring blade in the vertical direction.

13. The method according to claim 1, wherein the one or more stirring blades are configured to move (ii) reciprocally in the horizontal direction or the forward and reverse rotation direction.

14. A method for producing a platelet preparation, which comprises:
   the step of producing platelets in megakaryocyte cells by the method according to claim 8, and collecting the platelets from a culture; and
   the step of removing a hematopoietic cell component other than platelets from the platelets.

15. A method for producing a blood preparation, which comprises:
   the step of producing a platelet preparation by the method according to claim 14; and
   the step of mixing the platelet preparation and another component to obtain a blood preparation.

* * * * *